US006300517B1

(12) United States Patent
Stelzer et al.

(10) Patent No.: US 6,300,517 B1
(45) Date of Patent: Oct. 9, 2001

(54) PHOSPHINE LIGANDS WITH AMINO ACID GROUPS, METHOD FOR THEIR PRODUCTION AND USE THEREOF AS CATALYST COMPONENTS

(75) Inventors: Othmar Stelzer; Michael Tepper, both of Wuppertal (DE)

(73) Assignee: Celanese GmbH (DE)

( * ) Notice: Subject to any disclaimer, the term of this patent is extended or adjusted under 35 U.S.C. 154(b) by 0 days.

(21) Appl. No.: 09/367,191

(22) PCT Filed: Feb. 3, 1998

(86) PCT No.: PCT/EP98/00555

§ 371 Date: Dec. 10, 1999

§ 102(e) Date: Dec. 10, 1999

(87) PCT Pub. No.: WO98/34939

PCT Pub. Date: Aug. 13, 1998

(30) Foreign Application Priority Data

Feb. 7, 1997 (DE) .............................................. 197 04 491

(51) Int. Cl.[7] .................................................... C07C 53/34
(52) U.S. Cl. ........................... 562/496; 562/443; 560/105
(58) Field of Search ..................................... 562/496, 443; 560/105

(56) References Cited

PUBLICATIONS

Gilbertson et al., "Palladium . . . Amino Acids", J. Org. Chem. vol. 61, 1996, pp. 2922–2923.
Tepper et al, "A Systematic . . . Moieties", Tetrahedron Letters, vol. 38, No. 13, Mar. 1997, pp. 2257–2258.

Primary Examiner—Paul J. Killos
(74) Attorney, Agent, or Firm—Bierman, Muserlian and Lucas

(57) ABSTRACT

A description is given of new chiral phosphine ligands containing amino acid groups and having the formula I

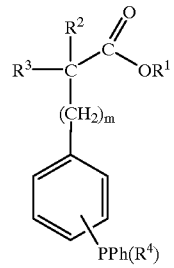

where
$R^1$ is hydrogen, a $C_1$–$C_7$-alkyl radical, a $C_6$–$C_{10}$-aryl radical or a monovalent metal, preferably sodium or potassium,
$R^2$ is hydrogen or a $C_1$–$C_7$-alkyl radical,
$R^3$ is hydrogen or an —$NR^5R^6$ radical, where $R^5$ and $R^6$ are identical or different and are hydrogen or $C_1$–$C_7$-alkyl or $C_6$–$C_{10}$-aryl radicals,
m is 0 or 1,
with the exception of the compounds in which $R^5$ and $R^6$ are hydrogen and at the same time $R^2$ is hydrogen, $R^4$ is phenyl and $R^1$ is methyl or benzyl and a process for their preparation.

These phosphine ligands are suitable as constituents of metal complexes which can be used as catalysts for reactions to form C—C, C—H, C—N, C—Si or C=O bonds.

10 Claims, No Drawings

PHOSPHINE LIGANDS WITH AMINO ACID GROUPS, METHOD FOR THEIR PRODUCTION AND USE THEREOF AS CATALYST COMPONENTS

The present invention relates to new chiral phosphine ligands containing amino acid groups, a process for preparing them and their use as catalyst constituents.

Phosphines have generally found a wide variety of uses in industry. They are suitable, for example, as antioxidants, metal extractants, flame retardant impregnants, stabilizers for olefins and trioxane, as starting compounds for Wittig reagents and as ligands for metal complex catalysts. Owing to their wide variety of forms, they also represent intermediates for the preparation of further organic compounds which may or may not contain phosphorus.

Since the phosphines contain a trivalent phosphorus atom in the molecule, they display complexing properties toward numerous metals and metal ions, particularly those from the transition series, which can be utilized for preparing corresponding metal complex catalysts which are employed in industrial processes.

Of particular importance is the development of ligands for catalyst systems which are used, for example, in the hydroformylation of olefins. Here, catalyst systems containing tertiary phosphines or phosphites as ligands have been found to be particularly useful.

Further phosphines which are of interest are those which are suitable for preparing chiral metal complexes. Examples of known phosphines of this type are the diphosphine S,S-2,4-bis[bis-(p-N,N-dimethylamino-phenyl)phosphino] pentane (Catalysis Letters 5 (1990) 183–188) and also N,N-dimethyl-[2-(diphenylphosphino)phenyl]-1(R)-ethylamine (Can. J. Chem. 64, (1986), 1930–1935). The Pt and Rh complexes of 2S,4S-(N-tert-butoxycarbonyl)-4-diphenylphosphino-2-[(di-tert-butylphosphino)methyl]-pyrrolidines and the corresponding dibenzophospholyl derivatives are active catalysts for the enantioselective hydroformylation of vinylaromatics and the enantioselective hydrogenation of prochiral olefins (Organometallics, 10 (1991), 1183–1189; J. Org. Chem. 45 (1990), 4728–4739). Rh(I) complexes of amphiphilic bidentate phosphines such as 2,2'-bis[phenyl(3-pyridyl)phosphinomethyl]-1,1'-biphenyl have been used for the hydroformylation of 1-octene. Owing to their amphiphilic character, these ligands can be recovered from the reaction mixtures by acid extraction (J. Chem. Soc., Dalton Trans. (1996), 2143–2154). Thiophosphorylprolines, thiophosphorylphenylglycines and thiophosphorylphenylalanines have been used as building blocks for the synthesis of phosphinyl-substituted peptides. Their Rh(I) complexes are of interest as novel bioconjugated and immobilized catalysts (Angew. Chem., 108 (1996), 963–966; J. Org. Chem. 61, (1996), 2922–2923).

In view of the particular importance of chiral phosphines, there is interest in preparing new compounds of this group, not only to supplement the range of possible applications but also to enrich and expand the range by varying material properties and structural features.

This object is achieved by compounds of the formula I

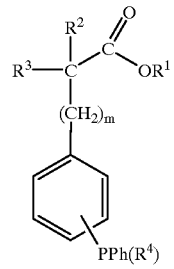

I where
$R^1$ is hydrogen, a $C_1$–$C_7$-alkyl radical, a $C_6$–$C_{10}$-aryl radical or a monovalent metal, preferably sodium or potassium,
$R^2$ is hydrogen or a $C_1$–$C_7$-alkyl radical,
$R^3$ is hydrogen or an —$NR^5R^6$ radical, where $R^5$ and $R^6$ are identical or different and are hydrogen or $C_1$–$C_7$-alkyl or $C_6$–$C_{10}$-aryl radicals,
$R^4$ is a $C_1$–$C_7$-alkyl or $C_6$–$C_{10}$-aryl radical and
m is 0 or 1.

Preferred compounds of the formula I are phosphinophenyl-substituted amino acids of the formula II based on phenylglycine

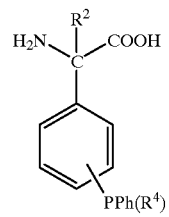

II where $R^2$ is hydrogen or methyl and $R^4$ is a $C_1$–$C_7$-alkyl or phenyl radical and the phosphinophenyl radical —PPh($R^4$) is located in the ortho or para position relative to the amino acid substituent —$C(NH_2)(R^2)$ (COOH).

As compounds of the formula I, preference is also given to phosphinophenyl-substituted amino acids of the formula III based on phenylalanine

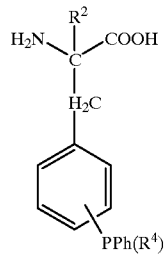

III where $R^2$ is hydrogen or a $C_1$–$C_7$-alkyl radical, in particular methyl, and $R^4$ is a $C_1$–$C_7$-alkyl or phenyl radical and the phosphinophenyl radical —PPh($R^4$) is located in the ortho or para position relative to the amino acid substituent —$CH_2$—$C(NH_2)(R^2)$(COOH).

The invention also provides a process for preparing compounds of the formula I by reaction of fluorophenyl-substituted compounds of the formula IV

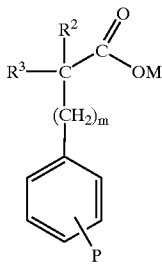

IV where
R² is hydrogen or a $C_1$–$C_7$-alkyl radical,
R³ is hydrogen or an —NR⁵R⁶ radical, where R⁵ and R⁶ are identical or different and are hydrogen or $C_1$–$C_7$-alkyl or aryl radicals,
m is 0 or 1 and
M is sodium or potassium,
with a phosphide of the formula V Ph(R⁴)PM    V where
R⁴ is a $C_1$–$C_7$-alkyl or $C_6$–$C_{10}$-aryl radical, in particular a phenyl radical, and
M is sodium or potassium,
and subsequent acid hydrolysis of the reaction mixture.

The reaction is usually carried out in an organic polar aprotic solvent such as 1,2-dimethoxyethane or tetrahydrofuran at a temperature of 80–120° C.

Preference is given to reacting sodium or potassium salts of 4-fluoro-α-phenylglycine (IVa), 4-fluoro-α-phenyl-α-methylglycine (IVb) and β-(4-fluorophenyl)-α-alanine (IVc) as compounds of the formula IV with the potassium phosphides Ph(R⁴)PK as compounds of the formula V, where R⁴ is a $C_1$–$C_7$-alkyl or phenyl radical.

While the sodium and potassium salts of 4-fluoro-α-phenylglycine (IVa) and β-(4-fluorophenyl)-α-alanine (IVc) are commercially available substances, the sodium or potassium salts of 4-fluoro-α-phenyl-α-methylglycine (IVb) can be prepared via a Bucherer reaction by reacting 4-fluoroacetophenone with potassium cyanide and ammonium carbonate to form a hydantoin of the formula VI as intermediate,

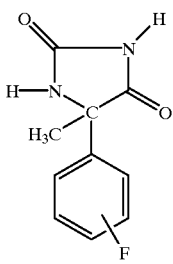

VI which is hydrolyzed using aqueous sodium hydroxide.

The novel compounds of the formula I are suitable as ligands for metal complexes which can be used as catalysts for reactions to form C—C, C—H, C—N, C—Si or C=O bonds.

EXAMPLE 1

Preparation of 2-diphenylphosphino-α-phenylglycine

A solution of 3.07 g (16.5 mmol) of diphenylphosphine in 60 ml of 1,2-dimethoxyethane was admixed with 0.64 g (16.5 mmol) of potassium. After the metallation reaction was complete, 3.0 g (15.7 mmol) of sodium 2-(2-fluorophenyl)glycinate were added and the reaction mixture was heated at 80° C. for 3 hours. Subsequently, 10 ml of methanol were added and the volatile constituents were removed at 80° C. at a pressure of $10^{-2}$ bar. The residue obtained was suspended in 500 ml of dilute aqueous hydrochloric acid (pH=4) and filtered, and then dried at 20° C. and $10^{-2}$ bar. The yield was 4.7 g (89%). For the further work-up, the product was recrystallized from a 3:1 mixture of water and methanol. The $^1H$, $^{13}C\{^1H\}$ and $^{31}P\{^1H\}$ NMR spectra were recorded on a Bruker AC 250 spectrometer; the mass spectra were recorded on a Varian MAT 311 A instrument.

Elemental analysis $C_{70}H_{18}NO_2P$. $2H_2O$ (371.49)

| | | | |
|---|---|---|---|
| Calculated | C 64.68 | H 5.97 | N 3.77 |
| Found | C 64.74 | H 5.95 | N 3.84 |

$^{31}P\{^1H\}$ NMR δP=−9.6 ppm
$^{13}C\{^1H\}$ NMR: (δ in ppm): 137.8 (9.7), 137.4 (8.9), 134.9 (19.2), 134.6
(18.8), 129.7 (6.8), 129.6 (6.7), 130.0, 129.8, 138.4 (13.7), 142.2 (27.2),
130.1, 131.2, 128.6 (4.7), 136.1 (1.3), 57.6 (27.7, CH), 179.8 (COOH)
MS: 335 (M⁺), 291 (M⁺−CO₂)

EXAMPLE 2

Preparation of 2-(methylphenyl)phosphino-α-phenylglycine

A solution of 2.11 g (17.0 mmol) of methylphenylphosphine in 20 ml of 1,2-dimethoxyethane was admixed with 0.67 g (17.0 mmol) of potassium metal. After the metallation reaction was complete, 3.0 g (15.7 mmol) of sodium 2-(2-fluorophenyl)glycinate were added and the reaction mixture was heated at 80° C. for 0.5 hour. Subsequently, excess potassium phenylmethylphosphide was hydrolyzed by addition of 10 ml of methanol and the volatile constituents were taken off from the reaction mixture under reduced pressure (80° C., 0.01 mbar). The residue was extracted with 50 ml of ether, dissolved in 500 ml of water and the pH was adjusted to about 4 by addition of 10% strength hydrochloric acid. The 2-(methylphenyl)phosphino-α-phenylglycine obtained as colorless precipitate was filtered off and dried under reduced pressure. The yield was 3.46 g (81%). For further purification, the product was recrystallized from methanol/water (1:1).

Elemental analysis $C_{15}H_{16}NO_2P$. $H_2O$ (291.3)

| | | | |
|---|---|---|---|
| Calculated | C 61.85 | H 6.23 | N 4.81 |
| Found | C 62.43 | H 6.55 | N 4.75 |

$^{31}$P {$^{1}$H} NMR δP=−31.3, −32.3 ppm $^{13}$C {$^{1}$H} NMR: δC(CH(NH$_2$)(COOH))=59.8 (24.1), 59.1 (26.2); δC(COOH)=180.3, 179.9 ppm (coupling constants "J(PC) in Hz in brackets)

MS: 229 (M$^+$—CO$_2$), 214 (M$^+$—CO$_2$—CH$_3$)

What is claimed is:

1. A compound of the formula I

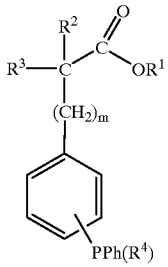

where

R$^1$ is hydrogen, a C$_1$–C$_7$-alkyl radical, a C$_6$–C$_{10}$-aryl radical or a monovalent metal, preferably sodium or potassium, R$^2$ is hydrogen or a C$_1$–C$_7$-alkyl radical, R$^3$ is hydrogen or an —NR$^5$R$^6$ radical, where R$^5$ and R$^6$ are identical or different and are hydrogen or C$_1$–C$_7$-alkyl or C$_6$–C$_{10}$-aryl radicals, R$^4$ is a C$_1$–C$_7$-alkyl or C$_6$–C$_{10}$-aryl radical and m is 0 or 1.

2. A compound as claimed in claim 1 which is a phosphinophenyl-substituted amino acid of the formula II based on phenylglycine,

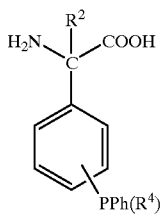

where R$^2$ is hydrogen or methyl and R$^4$ is a C$_1$–C$_7$-alkyl or phenyl radical and the phosphinophenyl radical —PPh(R$^4$) is located in the ortho or para position relative to the amino acid substituent —C(NH$_2$)(R$^2$)(COOH).

3. A compound as claimed in claim 1 which is a phosphinophenyl-substituted amino acid of the formula III based on phenylalanine,

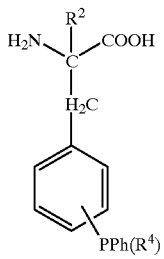

where R$^2$ is hydrogen or a C$_1$–C$_7$-alkyl radical, in particular methyl, and R$^4$ is a C$_1$–C$_7$-alkyl or phenyl radical and the phosphinophenyl radical —PPh(R$^4$) is located in the ortho or para position relative to the amino acid substituent —CH$_2$—C(NH$_2$)(R$^2$)(COOH).

4. A process for preparing compounds as claimed in any one of claims 1–3 by reaction of fluorophenyl-substituted compounds of the formula IV

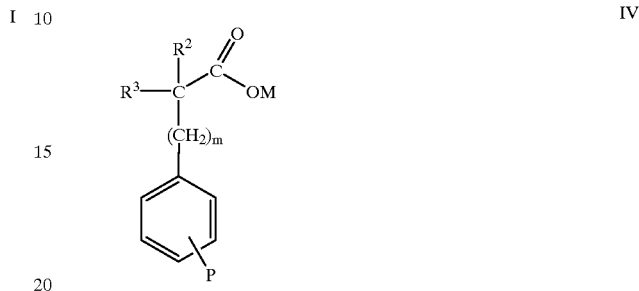

where

R$^2$ is hydrogen or a C$_1$–C$_7$-alkyl radical,

R$^3$ is hydrogen or an —NR$^5$R$^6$ radical, where R$^5$ and R$^6$ are identical or different and are hydrogen or C$_1$–C$_7$-alkyl or aryl radicals, m is 0 or 1 and M is sodium or potassium, with a phosphide of the formula V

Ph(R$^4$)PM     V where

R$^4$ is a C$_1$–C$_7$-alkyl or C$_6$–C$_{10}$-aryl radical, in particular a phenyl radical, and M is sodium or potassium, and subsequent acid hydrolysis of the reaction mixture.

5. The process as claimed in claim 4, wherein the reaction is carried out in an organic polar aprotic solvent, preferably 1,2-dimethoxyethane or tetrahydrofuran, at a temperature of 80–120° C.

6. The process as claimed in claim 4 or 5, wherein sodium or potassium salts of 4-fluoro-α-phenylglycine (IVa), 4-fluoro-α-phenyl-α-methylglycine (IVb) or β-(4-fluorophenyl)-α-alanine (IVc) as compounds of the formula IV are reacted with the potassium phosphides Ph(R$^4$)PK as compounds of the formula V, where R$^4$ is a C$_1$–C$_7$-alkyl or phenyl radical.

7. The process of claim 4 wherein R' is sodium or potassium.

8. The process of claim 4 wherein R$_4$ is phenyl.

9. The process of claim 5 wherein the aprotic solvent is 1,2-dimethoxyethane or tetrahydrofuran.

10. A metal complex containing a ligand of claim 1.

* * * * *